United States Patent [19]

Auerbach

[11] Patent Number: 4,792,568
[45] Date of Patent: Dec. 20, 1988

[54] ARYL PYRROLES AS USEFUL ANTIALLERGY COMPOUNDS

[75] Inventor: Joseph Auerbach, Brooklyn, N.Y.

[73] Assignee: Rorer Pharmaceutical Corporation, Fort Washington, Pa.

[21] Appl. No.: 851,989

[22] Filed: Apr. 14, 1986

[51] Int. Cl.$^4$ .................. A61K 31/40; C07D 207/325
[52] U.S. Cl. ..................... 514/423; 514/427; 544/372; 546/152; 546/208; 546/275; 548/189; 548/217; 548/233; 548/517; 548/518; 548/527; 548/530; 548/540; 548/562; 548/563
[58] Field of Search .............. 548/563, 530, 562, 540; 514/427, 423

[56] References Cited

U.S. PATENT DOCUMENTS 2,986,564  5/1961  Rips ....................................... 548/563

Primary Examiner—Joseph Paul Brust

[57] ABSTRACT

This invention relates to new lipoxygenase inhibitors possessing anti-inflammatory and anti-allergic properties. The present new compounds are of the formula:

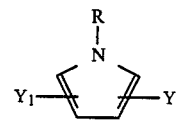

and salts thereof; wherein,

R is hydrogen, lower alkyl, lower alkenyl, lower alkynyl, lower aralkyl, phenyl, naphthyl, or a nitrogen oxygen or sulfur heterocyclic; and $Y_1$ and Y are independently hydrogen, lower alkyl, hydroxy, lower alkoxy, aryloxy, lower aralkoxy, aryl, lower aralkyl, carboxy, lower carbalkoxy, lower carbaralkoxy, carbaryloxy, formyl, or alkyl, alkenyl or alkynyl containing up to 6 carbon atoms in the principal chain and up to a total of 10 carbon atoms;

provided that when Y and $Y_1$ are both hydrogen or when $Y_1$ is hydrogen and Y is CHO, the R is other than hydrogen, unsubstituted phenyl, or lower alkyl.

10 Claims, No Drawings

ARYL PYRROLES AS USEFUL ANTIALLERGY COMPOUNDS

This invention relates to the use of certain chemical compounds possessing valuable pharmaceutical activity, particularly as lipoxygenase inhibitors possessing anti-inflammatory and anti-allergic properties. This invention also relates to novel chemical compounds which also possess these same characteristics.

SUMMARY OF THE INVENTION

The present new compounds are of the formula:

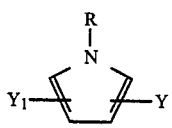

and salts thereof; wherein,

R is hydrogen, lower alkyl, lower alkenyl, lower alkynyl, lower aralkyl, phenyl, naphthyl, or a nitrogen, oxygen or sulfur heterocyclic; and $Y_1$ and Y are independently hydrogen, hydroxy, lower alkoxy, aryloxy, lower aralkoxy, aryl, lower aralkyl, carboxy, lower carbalkoxy, lower carbaralkoxy, carbaryloxy, formyl, or alkyl, alkenyl or alkynyl containing up to 6 carbon atoms in the principal chain and up to a total of 10 carbon atoms;

provided that when Y and $Y_1$ are both hydrogen or when $Y_1$ is H and Y is CHO, then R is other than hydrogen, unsubstituted phenyl or lower alkyl.

In addition, the present invention is concerned with the therapeutic composition comprising as an active ingredient a compound of the formula:

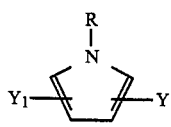

wherein

R is hydrogen, lower alkyl, lower alkenyl, lower alkenyl, lower alkynyl, lower aralkyl, phenyl, naphthyl or a nitrogen, oxygen or sulfur heterocyclic; and $Y_1$ and Y are independently hydrogen, hydroxy, lower alkoxy, aryloxy, lower aralkoxy, aryl, lower aralkyl, carboxy, lower carbalkoxy, lower carbaralkoxy, carbaryloxy, formyl or alkyl, alkenyl or alkynyl chain containing up to 6 carbon atoms in the principal chain and up to a total of 10 carbon atoms.

The heterocyclic groups exemplary of R are 5-10 membered rings containing at least one oxygen, sulfur or nitrogen and include the so-called benzoheterocyclic rings. Exemplary heterocyclics include furan, thiophene, pyrrole, piperidine, dihydrofuran, pyridine, thiazole, piperazine, oxazole, benzofuran, tetrahydroquinoline, quinoline, indole, dihydroindole, benzothiophene, dihydrobenzothiophene, benzoxazole, and similar heterocyclics.

The aryl moieties of R, $Y_1$ and Y include phenyl or α- or β-naphthyl, etc.

In the foregoing, when R is phenyl, naphthyl or a nitrogen, oxygen, or sulfur heterocyclic, it may be mono- or di-substituted with a variety of substituents such as hydrogen, lower alkyl, aryl, lower aralkyl, hydroxy, halo, lower alkoxy, lower aryloxy, lower aralkoxy, carboxy, lower carbalkoxy, carbaryloxy, lower carbaralkoxy, lower alkanoyl, formyl, nitrilo, amino, aminoloweralkyl, lower alkylamino diloweralkyl amino, carboxamide, aryloxy, nitro, sulfonyl, sulfonamide, mercapto or alkylthio.

The alkyl groups either alone or within the various substituents defined hereinbefore are preferably lower alkyl which may be straight or branched chain and include methyl, ethyl, propyl, isopropyl, butyl, isobutyl, amyl, hexyl and the like.

The alkyl, alkenyl and alkynyl groups represented by Y and $Y_1$ can be normal or branched chains. Said hydrocarbyl chains preferably contain 2 to 6 carbon atoms in the principal chain and up to a total of 10 carbon atoms. The alkenyl and alkynyl groups may contain up to two double or triple bonds, but these multiple bonds may not be attached directly to the pyrrole ring. In addition, these chains may be mono or di-substituted with a variety of substituents such as hydrogen, lower alkyl, aryl, lower aralkyl, hydroxy, lower alkoxy, carboxy, lower-carbalkoxy, lower carbaralkoxy, carbaryloxy, formyl, lower alkanoyl, nitrilo, amino, aminoloweralkyl, loweralkylamino, diloweralkylamino, carboxamide, nitro, sulfonyl, sulfonamide, mercapto, alkylthio or lower alkyl carbonyl.

Preferred compounds and therapeutic compositions are those wherein R is phenyl which is substituted with hydrogen, hydroxy, aryloxy, loweralkoxy, or loweraralkoxy, Y and $Y_1$ are independently hydrogen, formyl, an alkyl group which is substituted with hydroxy or hydrogen on the alpha carbon to the pyrrole or an alkenylene group containing 1 double bond which is substituted on the omega carbon atom with carboxy or carbalkoxy. The preferred substitution on the phenyl ring in R is hydrogen or phenoxy.

Especially preferred compounds of the present invention have the formula

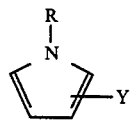

wherein R and Y are as defined heretofore. In particular, these especially preferred compounds are those wherein R is phenyl which is substituted with hydrogen or phenoxy, and Y is hydrogen, formyl, an alkyl group containing up to 6 carbon atoms which is substituted with hydroxy or hydrogen on the alpha carbon to the pyrrole, or an alkenyl group containing 1 double bond and containing up to 6 carbon atoms, which is substituted with carbalkoxy on the omega carbon. Especially preferred carbalkoxy groups are —COOMe.

Illustrative preferred compounds include:
2-(5-Carbomethoxy-1-pentenyl)-1-phenylpyrrole
3-(5-Carbomethoxy-1-pentenyl)-1-phenylpyrrole
2-(3-Carbomethoxy-2-propenyl)-1-phenylpyrrole
3-(3-Carbomethoxy-2-propenyl)-1-phenylpyrrole
2-(4-Carbomethoxypropyl)-1-phenylpyrrole
2-(1-Hydroxyethyl)-1-phenylpyrrole
2-(1-Hydroxyethyl)-1-phenylpyrrole
2-(Benzylhydroxy)-1-phenylpyrrole
1-(3-Phenoxyphenyl)pyrrole-2-aldehyde
1-(3-Phenoxyphenyl)pyrrole-3-aldehyde
2-(1-Hydroxyhexyl)-1-(3-phenoxyphenyl)pyrrole
3-(1-Hydroxyhexyl)-1-phenylpyrrole 3-(1-Hydroxyhexyl)-1-(3-phenoxyphenyl)pyrrole Active ingredients in the therapeutic composition include the following preferred compounds:
2-(5-carbomethoxy-1-pentenyl)-1-phenylpyrrole
3-(5-carbomethoxy-1-pentenyl)-1-phenylpyrrole
2-(3-carbomethoxy-2-propenyl)-1-phenylpyrrole
3-(3-carbomethoxy-2-propenyl)-1-phenylpyrrole
2-(4-carbomethoxypropyl)-1-phenylpyrrole
2-(1-hydroxyethyl)-1-phenylpyrrole
2-(1-hydroxyhexyl)-1-phenylpyrrole
2-(benzylhydroxy)-1-phenylpyrrole
1-(3-phenoxyphenyl)pyrrole
1-(3-phenoxyphenyl)pyrrole-2-aldehyde
1-(3-phenoxyphenyl)pyrrole-3-aldehyde
2-(1-hydroxyhexyl)-1-(3-phenoxyphenyl)pyrrole
1-phenylpyrrole
1-phenyl-2-formylpyrrole
1-phenyl-3-formylpyrrole
3-(1-hydroxyhexyl)-1-phenylpyrrole
3-(1-hydroxyhexyl)-1-(3-phenoxyphenyl)pyrrole The compounds of the present invention may contain one or more asymmetric carbon atoms and may exist in racemic and optionally active forms. All of these compounds are contemplated to be within the scope of the present invention.

The present compounds can be prepared by art recognized procedures from known compounds or readily preparable intermediates. An exemplary general procedure, forming a useful intermediate which is itself encompassed within the scope of the invention, is as follows:

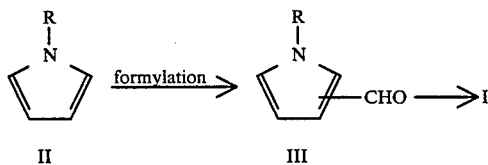

wherein R is as defined hereinabove. A pyrrole is formylated to form the formyl-pyrrole derivative. The pyrrole is formulated with formylating agents known in the art. For example, under the conditions of the Vilsmeier-Haack reaction, the pyrrole can be formulated with phosphorous exychloride in the presence of disubstituted formamides, e.g., dimethylformamides. The reaction is carried out in a solvent that will dissolve both reactants and is inert to both as well. Solvents such as dioxane, ether, tetrahydrofuran, methylene chloride, chloroform, 1,2-dichloroethane, and the like can be employed. The reaction is initially normally effected at a near 0° C., although temperatures from −78° C. to room temperature can be employed. After the exothermic reaction has subsided, temperatures from 0° C. to reflux temperature can be used, although temperatures from about 0° to about 40° C. are preferred.

Other reagents and conditions are known in the art to effect formylation. Other reagents include carbon monoxide and hydrogen chloride in the presence of a Lewis acid, such as $AlCl_3$, under the Gatterman-Koch reaction condition; $Zn(CN)_2$ and a strong acid, e.g., HCl under the Gatterman reaction condition; formyl fluoride in the presence of a Lewis acid, e.g., $BF_3$; dichloromethyl methyl ether in the presence of Friedel Crafts catalysts; chloroform and hydroxide ion under the Reimer-Tiemann reaction conditions; and the like.

The alkyl, alkenyl and alkynyl groups are added to compounds of Formula III by procedures known in the art. For example, the formyl-pyrrole of Formula III is reacted with a Grignard reagent in order to form compounds of Formula IV:

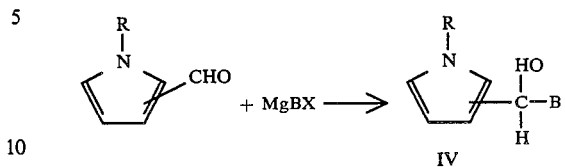

wherein R is as defined above, X is halogen (Cl, Br, I, or F) and B is an alkyl group containing 1 to 5 carbon atoms in the principal chain or an alkenyl or alkynyl group containing 2 to 5 carbon atoms and the double bond is not in the 1-position, i.e., in the position adjacent to the carbinol. The reaction is normally effected at or near room temperatures, although temperatures from 0° C. up to the reflux temperature of the reaction medium can be employed. The reaction is carried out in a solvent that will dissolve both reactants and is inert to both reactants and products.

Solvents include diethyl ether, tetrahydrofuran, dioxane, and the like. In the case wherein Y of Formula I contains a hydroxy group in the position to the pyrrole, then

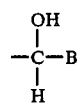

group is Y.

By substitution and conversion reactions, compounds of Formula IV are converted to other groups representative of Y. For example, by using art recognized procedures, compounds of Formula IV can be converted to the 1-alkenes through acid dehydration and to the alkyl derivatives by hydrogenation of the 1-alkene. Through isomerization techniques known in the art, the multiple bonds can also "migrate" on the chain to different positions.

Various substituents on the present new compounds, e.g., as defined in R, Y, and $Y_1$ can be present in the starting compounds, added to any one of the intermediates or added after formation of the known products by the known methods of substitution or conversion reactions.

Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

If substituents on the groups are themselves reactive under the reaction conditions, then these substituents can themselves be protected according to the techniques known in the art. A variety of protecting groups known in the art may be employed. Examples of many of these possible groups may be found in "protective Groups in Organic Synthesis", by T. W. Green, John Wiley and Sons, 1981. For example, in the Grignard reaction described hereinabove, if a carbonyl or carboxy group is present on R Y, then said group can be converted to 2-alkyl-1, 3-oxazoline, which is stable to Grignard reagents.

The present new compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, malic, tartaric and the like which are pharmaceutically acceptable. Basic salts for pharmaceutical use are the Na, K, Ca, and Mg salts.

The compounds of the present invention can be administered to the host in a variety of forms adapted to the chosen route of administration, e.g., orally, intravenously, rectally, intramuscularly or subcutaneous, topically or inhalation routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, suppositories, capsules and the like may also contain the following: A binder such as gum tragacanth, acacia, corn starch or gelatin; excipients such as dicalcium phosphate; a disintegrating agent such as corn starch, potato starch, alginic acid and the like, a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose, as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The following examples further illustrate the invention.

EXAMPLES 1 AND 2

Example 1

1-(3-Phenoxyphenyl)-pyrrole-2-aldehyde

Example 2

1-(3-Phenoxyphenyl)-pyrrole-3-aldehyde

Phosphorous oxychloride (0.3 mL, 100 mmol) was added to a solution of DMF (7.3 g, 100 mmol) in 25 mL of 1,2-dichloroethane at such a rate as to keep the internal reaction temperature below 10° C. To the mixture at 5° C. was added 3-phenoxypyrrole (21.1 g, 89.7 mmol). After the exothermic reaction subsided the mixture was stirred at 5° C. for 0.5 h and 35° C. for 0.5 h and 54.4 g (400 mmol) of sodium acetate trihydrate in 100 mL of water was added. The mixture was heated at steambath temperatures for 25 min., cooled and extracted with ether. The etherate was cross washed with 2N NaOH solution, brine, filtered, dried with MgSO$_4$, filtered and evaporated to dryness. The product was isolated by column chromatography on silica gel (for dry column chromatography) eluting preferably with 10% ethylacetate-hexane (v/v). After combining appropriate fractions and after solvent removal, 15.1 g of oily 1-(3-phenoxyphenyl)-pyrrole-2-aldehyde, and 1.66 g of 1-(3-phenoxyphenyl)-pyrrole-3-aldehyde as an oil was isolated. The products gave correct spectral identification.

Similarly, by using the appropriate starting materials, the following compounds can also be prepared:
1-phenyl-2-formylpyrrole
1-phenyl-3-formylpyrrole

EXAMPLE 3

2-(1-Hydroxyhexyl)-1-(3-phenoxyphenyl)pyrrole

Magnesium turnings (2.4 g, 100 mmol) were activated with a crystal of iodine by heating under nitrogen the cooled magnesium and 6.1 g of 1-bromopentane (40 mmol, 99% purity) in 200 mL of ether. The reaction medium was heated to reflux and the reaction was self-sustaining. After 0.75 h the reaction was complete and the mixture was cooled to ice bath temperatures and 5 g of 1-(3-phenoxyphenyl)-pyrrole-2-aldehyde (19 mmol) in 25 mL of ether was added. The reaction was stirred for 1 h and poured into 500 ml of 1N $NH_4Cl$ solution. The product was extracted into ether and the ether was cross washed with 1 N $NH_4Cl$ solution. The etherate was separated, dried with $MgSO_4$ and filtered, and the solvent was evaporated, yielding 6.35 g of crude product. The product was column chromatographed three times on silica gel (for dry column chromatography) and finally on Florisil eluting with ether acetate/hexane (1:40, v/v). After solvent removal, there was obtained 1.1 g of the final product. The product gave correct elemental analysis and spectral identification.

EXAMPLE 4

3-(1-Hydroxyhexyl)-1-(3-phenoxyphenyl)pyrrole

Grignard reagent was prepared (from 0.5 g of Mg) as described in Example 3. Then 1.8 g of 1-(3-phenoxyphenyl)pyrrole-3-aldehyde in 15 mL of ether was added. The reaction was stirred for 1 h and then poured into 300 mL of 1 N $NH_4Cl$ solution. The product was extracted with ether and the combined organic solution was washed with $H_2O$, dried and evaporated to dryness. The crude product was purified by dry column chromatography to give 0.85 g of desired product as an oil.

EXAMPLE 5

2-(1-Hydroxyhexyl)-1-phenylpyrrole

Grignard reagent was prepared from 2.4 g of Mg and 7.6 g of 1-bromopentane as described in Example 3. 1-Phenylpyrrole-2-aldehyde 4.28 g in 25 mL of ether was added dropwise to the Grignard reaction mixture. Reaction was continued for 2 h at room temperature. The reaction mixture was worked up and purified as described earlier to give 5 g of oily product.

EXAMPLE 6

3-(1-Hydroxyhexyl)-1-phenylpyrrole

This compound was synthesized according to the procedure described in Example 3. Thus, starting from 2.2 g of 1-phenylpyrrole-3-aldehyde, 1.2 g of magnesium and 3.8 g of 1-bromopentane, 3 g of pure product was obtained as an oil.

Similarly, by using the appropriate starting materials, the following compounds were prepared:
2-(benzylhydroxy)-1-phenylpyrrole
2-(1-hydroxyethyl)-1-phenylpyrrole The compounds of the present invention have potent activity in regulating the activity of lipoxygenase and as such possess therapeutic value in the treatment of inflammatory conditions and allergic responses such as anaphlaxis and asthma.

Lipoxygeneases in mammals have been found in the lung, platelets, and white cells. They are enzymes capable of oxidizing arachidonic acid into hydroperoxyeicosatetraenoic acids (HPETEs) and their stable products hydroxyeicosatetraenoic acids (HETEs). Lipoxygeneases are classified according to the position in the arachidonic acid which is oxygenated. Platelets metabolize arachidonic acid and 12-HETE, while polymorphonuclear (PMN) leukocytes contain 5 to 15 lipoxygenases. It is known that 12-HETE and 5, 12-diHETE are chemotactic for human neutrophils and eosinophils, and may augment the inflammation process. 5-HPETE is known to be a precursor of a slow-reacting substance of anaphylaxis (SRS-A). The SRS family of molecules, such as leukotrienes B, C, and D, have been shown to be potent bronchoconstrictors (see, NATURE 288, 484–486 (1980)).

The following protocol describes an assay to detect inhibitors of the lipoxygenase. Such inhibitors are believed to be capable of modulating the biosynthesis of the leukotrienes, a property believed to be useful in treating asthma and inflammatory disease states.

Protocol for Detecting Inhibitors of the Lipxoygenease Pathway

A suspension of rat neutrophils in buffer is incubated for 3 minutes at 30° C. with [$^{14}$C]-arachidonic acid (AA) and Calcium Ionophore A23187. Citric acid (2M) is used to quench the reaction. Following the addition of a trace amount of ($^3$H)-5-HETE together with an excess of unlabeled 5-HETE to each tube, the mixture is extracted with chloroform/methanol. The organic layer is washed wth dilute acid and an aliquot is transferred to glass tubes and dried. The residue is dissolved in a small volume of chloroform and an aliquot is spotted on silica gel TLC sheets, which are developed with an ethyl acetate/isooctane/water/acetic acid solvent system. The 5-HETE spots are visualized with iodine, cut out and placed in scintillation vials for counting. After adjusting for the extraction efficiency, the amount (pmole) of [$^{14}$C]-5-HETE in each of the tubes is quantitated. The net pmoles of 5-HETE are obtained by subtracting the pmoles of 5-HETE in the tubes containing buffer alone (blank) from the pmoles of 5-HETE in the tubes containing buffer and cells (control). The ability of the test compounds to modulate the activity of this enzyme is determined by a decrease or increase in the net amount of 5-HETE produced.

The following shows either the concentration required for inhibition of the 5-lipoxygenase (5-LOX/$I_{50}$ $\mu$M) or the relative activity of 10 $\mu$M for representative compounds of Examples 1–6.

| | | |
|---|---|---|
| Example 1 | 10 $\mu$M | medium |
| Example 2 | 10 $\mu$M | medium |
| Example 3 | $I_{50} =$ | 7 $\mu$M |
| Example 4 | $I_{50} =$ | 4 $\mu$M |
| Example 5 | $I_{50} =$ | 20 $\mu$M |
| Example 6 | 10 $\mu$M | medium |

Protocol for SRS-A (Slow-Reacting Substance of Anaphylaxis) Antagonists (SALTI)

Peripheral strips of guinea pig lungs are prepared and hung in tissue baths (Metro #ME-5505, 10 ml) according to the published procedure (Pro. Nat'l. Acad. Sci., U.S.A. Volume 77, pp. 4354–4358, 1980). The strips are thoroughly rinsed in Assay Buffer and then connected with surgical silk thread to the support rods from the tissue baths. The rods are adjusted in the baths and the strips connected to the pressure transducers (Grass FT 103 or Gould UC-3_. The tissue baths are aerated with 95% oxygen-5% carbon dioxide and maintained at 37° C. The Assay Buffer has been made as follows:

For each liter of buffer the following are added to approximately 800 ml of water distilled in glass: 6.87 g NaCl, 0.4 g KCl, 21 g $NaHCO_3$, 0.14 g $NaH_2PO_4H_2O$, 0.21 g $MgSO_4$ $7H_2O$, and 2.0 g D-glucose. Tehn a solution of 0.368 g $CaCl_2$ $2H_2O$ in 100 ml glass-distilled water is slowly added to the buffer. Sufficient water is added to adjust the volume to one liter, and the solution is aerated with 95% oxygen—5% carbon dioxide. Usually 10 liters of buffer are used for an experiment with 4 tissues.

After the tissues have been repeatedly washed and allowed to equilibrate in the tissue bath, they are challenged with 1 μM histamine. After maximum contractions have been obtained, the tissues are washed, and allowed to relax back to baseline tension. This histamine challenge procedure is repeated at least 1 to 2 more times ot obtain a repeatable control response. The average response to 1 μM histamine for each tissue is used to normalize all other challenges.

Responses of each tissue to a predetermined concentration of leukotriene are then obtained. Usually test compounds are examined initially at 30 μM on resting tension of the tissues without any added agonist or antagonist to determine if the compound has any possible intrinsic activity. The tissues are washed, and the test compound is added again. Leukotriene is added after the desired pre-incubation time. The intrinsic activity of the compounds and their effect on leukotriene-induced contractions are then recorded.

The concentration required for 50% inhibition of 0.2 nM leukotriene $C_4$-induced contraction of guinea pig peripheral strips for the compounds of the Examples 1 to 6 is as follows:

| Example 1 | $I_{50}$ = | 20 μM |
| Example 2 | $I_{50}$ = | 18 μM |
| Example 3 | Inactive | |
| Example 4 | Not tested | |
| Example 5 | Inactive | |
| Example 6 | Not tested | |

What is claimed is:

1. A thereapeutic composition for treating allergic condition in a mammal comprising:
an inert pharmaceutically acceptable carrier; and a compound of the formula

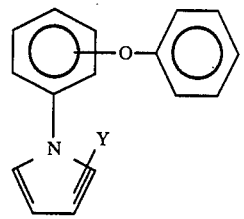

and its pharmaceutically acceptable salts, wherein Y is H, $C_{1-6}$ alkanoyl, $C_{1-6}$ alkyl or $C_{1-6}$ alkenyl containing one double bond not attached directly to the pyrole, wherein the alkyl may be substituted with hydroxy or $C_{1-6}$ alkoxy and the alkenyl may be substituted with carb-$C_{1-6}$-alkoxy.

2. A compound of the formula

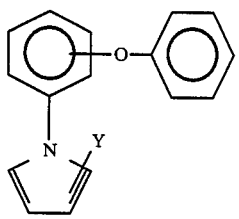

and its pharmaceutically acceptable salts, wherein Y is H, $C_{1-6}$ alkanoyl, $C_{1-6}$ alkyl or $C_{2-6}$ alkenyl containing one double bond not attached directly to the pyrole, wherein the alkyl may be substituted with hydroxy or $C_{1-6}$ alkoxy and the alkenyl may be substituted with carb-$C_{1-6}$-alkoxy.

3. A compound of claim 2 wherein the alkyl group is substituted with hydroxy on the alpha carbon to the pyrole or the alkenyl group is substituted with carb-$C_{1-6}$-alkoxy.

4. A compound of the formula

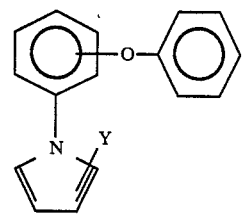

and its pharmaceutically acceptable salts, wherein Y is is CHO or $C_{1-6}$ alkyl substituted with hydroxy.

5. A method for treating allergic condition in a mammal comprising administering a therapeutically effective amount of a compound of claim 4.

6. The compound which is 1-(3-Phenoxyphenyl)pyrrole.

7. The compound which is 1-(3-Phenoxyphenyl)pyrrole-2-aldehyde.

8. The compound which is 1-(3-Phenoxyphenyl)pyrrole-3-aldehyde.

9. The compound which is 2-(1-Hydroxyhexyl)-1-(3-phenoxyphenyl)pyrrole.

10. The compound which is 3-(1-Hydroxyhexyl)-1-(3-phenoxyphenyl)pyrrole.

* * * * *